United States Patent
Buchholz et al.

(10) Patent No.: US 6,420,142 B1
(45) Date of Patent: Jul. 16, 2002

(54) METHOD FOR ENZYMATIC SPLITTING OF RUTINOSIDES

(75) Inventors: Herwig Buchholz, Frankfurt; Thomas Koppe, Darmstadt; Michael Schleehahn, Reichenbach, all of (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/830,287

(22) PCT Filed: Oct. 13, 1999

(86) PCT No.: PCT/EP99/07686

§ 371 (c)(1),
(2), (4) Date: Apr. 25, 2001

(87) PCT Pub. No.: WO00/26400

PCT Pub. Date: May 11, 2000

(30) Foreign Application Priority Data

Oct. 30, 1998 (DE) .......................................... 198 50 029

(51) Int. Cl.$^7$ ............................ C12P 19/58; C12P 19/02
(52) U.S. Cl. ............................. 435/77; 435/74; 435/105
(58) Field of Search ............................. 435/77, 74, 105

(56) References Cited

U.S. PATENT DOCUMENTS 4,772,334 A    9/1988    Kogyo

FOREIGN PATENT DOCUMENTS

| EP | 273076 | 7/1988 |
| EP | 317033 | 5/1989 |
| JP | 61185167 | 8/1986 |
| JP | 62000292 | 1/1987 |
| JP | 62000293 | 1/1987 |
| JP | 4099771 | 3/1992 |
| JP | 6199695 | 7/1994 |
| JP | 6248267 | 9/1994 |
| JP | 6261700 | 9/1994 |
| JP | 10095732 | 4/1998 |
| WO | WO 9944578 | 9/1999 |

OTHER PUBLICATIONS

Database WPI Section Ch, Week 198706 Derwent Publications Ltd., London, GB; Class B03, AN 1987–040883 XP002128152 & 62 000292 A (Kanegafuchi Chem KK), 6. Januar 1987 (Jan. 06, 1987).
Chemical Abstracts, vol. 122, No. 5, 30. Januar 1995 (Jan. 30, 1995) Columbus, Ohio, US; abstract No. 54685, Nakayama, Tsutomu Et At: "quercetin, kaempferol, catechin, and taxifolin as antioxidants for food preservation" XP002133790 & JP 06 248267 A (Esu Ai Ai Tekuno Risaachi Juge, Japan;Nakayama Tsutomu) Sep. 6,1994.
Chemical Abstracts, vol. 120, No. 3, 17. Januar 1994 (Jan. 17, 1994) Columbus, Ohio, US; abstract No. 29556, Herrmann, Karl: "Flavonoid antioxidants in food of plant origin" XP002133789 & Gordian (1993), 93(7–8), 108–11.
Chemical Abstracts, vol. 106, No. 25, 22. Juni 1987 (Jun. 22, 1987) Columbus, Ohio, US; abstract No. 212578, Sakai, Takuo: "Enzymic production of L–rhamnose" XP002128151 & JP 62 000293 A (Kanegafuchi Chemical Industry Co., Ltd., Japan) 6. Januar 1987 (Jan. 06, 1987).
Chemical Abstracts, vol. 128, No. 24, 15. Juni 1998 (Jun. 15, 1998) Columbus, Ohio, US; abstract No. 292169, Uchino, Keijirou Et Al: "Glycerophosphate dehydrogenase inhibitors containing flavonoids, and food additives and food containing them" XP002133791 & JP 10 095732 A (Nippon Flour Mills Co., Ltd., Japan) Apr. 14, 1998.
Database WPI Section Ch, Week 199433 Dewent Publications Ltd., London, GB; Class B05, AN 1994–269371 XP002133795 & JP 06 199695 A (Kato K), 19. Juli 1994 (Jul. 19, 1994).
Patent Abstracts of Japan vol. 011, No. 008 (C–396), 9. Januar 1987 (Jan. 09, 1987) & JP 61 185167 A (Kazuko Kawanishi), Aug. 18, 1986.
Patent Abstracts of Japan vol. 016, No. 338 (C–0965), 22. Juli 1992 (Jul. 22, 1992) & JP 04 099771 A (San Ei Chem Ind Ltd), 31. Maerz 1992 (Mar. 31, 1992).
Database WPI Section Ch, Week 199442 Derwent Publications Ltd., London, GB; Class D13, AN 1994–337365 XP002133793 & JP 06 261700 A (Toyo Seito KK), Sep. 20, 1994.
Chemical Abstracts, vol. 131, No. 12, Sep. 20 1999 Columbus, Ohio, US; abstract No. 157174, Karakaya, Sibel Et Al: "Quercetin, luteolin, apigenin and kaempferol contents of some foods" XP002133792 & Food Chem. (1999), 66(3), 289–292.

*Primary Examiner*—Herbert J. Lilling
(74) *Attorney, Agent, or Firm*—Millen, White, Zelano & Branigan, P.C.

(57) ABSTRACT

Disclosed is a method for enzymatic splitting of rutinosides, whereby rhamnose and/or corresponding glucopyranosides is/are obtained The inventive method is carried out in the presence of a solvent mixture made up of water and one or several organic solvents.

8 Claims, No Drawings

METHOD FOR ENZYMATIC SPLITTING OF RUTINOSIDES

The invention relates to a process for the enzymatic cleavage of rutinosides to obtain rhamnose and/or the corresponding glucopyranosides, the reaction being carried out in the presence of a solvent mixture of water and one or more organic solvents.

In the context of the present invention, rutinosides are designated as those compounds which contain a sugar-free constituent, to which a radical of the

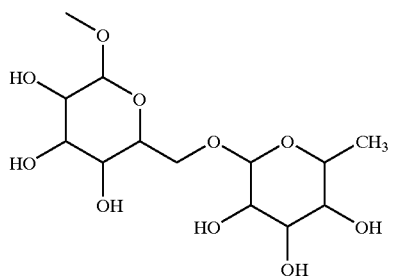
(I)

is bonded via a glycosidic bond. For example, the rutinosides are flavonoids having the bisglycosidic unit shown in formula I. Rhamnose and/or the corresponding glucopyranosides are produced from the rutinosides by the process according to the invention. The glucopyranosides are derived from the rutinosides in that, instead of the radical of the formula (I), they contain a radical of the formula (I*)

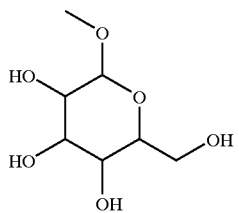
(I*)

bonded to the sugar-free constituent. For example, both rhamnose and isoquercetin can be obtained from rutin by the process according to the invention.

Rhamnose is a monosaccharide which is of widespread occurrence in nature, but usually only in small amounts. An important source of rhamnose is, for example, the glycosidic radicals of natural flavonoids such as rutin, from which the rhamnose can be obtained by glycoside cleavage. Rhamnose, for example, plays an important role as a starting substance for the preparation of synthetic aromatic substances such as furaneol.

Isoquercetin is a monoglycosidated flavonoid of the following structural formula (II)

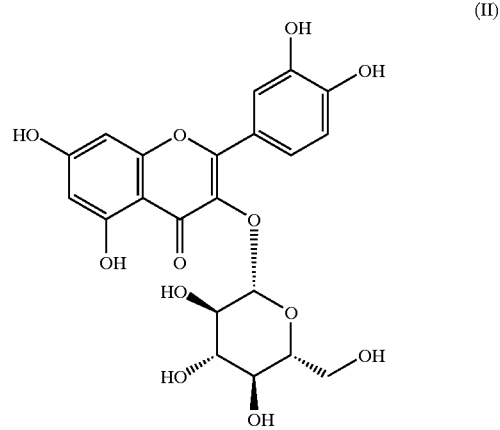
(II)

Flavonoids. (lat. flavus=yellow), which are widespread colorants in plants, are designated as being, for example, glycosides of flavones, to which the parent structure of flavone (2-phenyl-4H-1-benzopyran-4-one) is common.

The sugar-free constituent of the flavonoids is the so-called aglycone. Isoquercetin is, for example, a glycoside of the aglycone quercetin (2-(3,4-dihydroxyphenyl)-3,5,7-trihydroxy-4H-1-benzopyran-4-one), which differs from flavone by the presence of five hydroxyl groups. In isoquercetin, the carbohydrate radical glucose is bonded to the hydroxyl group in position 3 of the quercetin. Isoquercetin is designated, for example, as quercetin 3-O-β-D-glucopyranoside or 2-(3,4-dihydroxyphenyl)-3-(β-D-glucopyranosyloxy)-5,7-dihydroxy-4H-1-benzopyran-4-one. However, it is also known, for example, under the name hirsutrin.

Flavonoids and flavonoid mixtures are used, for example, in the foodstuffs and cosmetics industries and are increasingly gaining importance there. Particularly monoglycosidated flavonoids such as isoquercetin are distinguished by a good absorption capacity in the human body.

An example of a naturally occurring flavonoid having a bisglycosidic unit is rutin, which has the following structural formula (III):

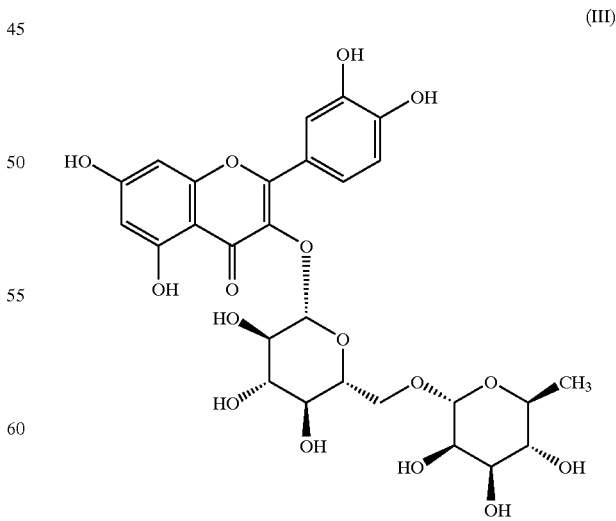
(III)

Rutin, like isoquercetin, is likewise a glycoside of the aglycone quercetin where the carbohydrate radical rutinose is bonded to the hydroxyl group in position 3 of the quercetin. The carbohydrate radical in rutin consists of a glucose unit linked in the 1 and 6 positions and a terminally bonded rhamnose or 6-deoxymannose unit. Rutin is designated, for example, as quercetin 3-O-β-D-rutinoside or 2-(3,4-dihydroxy-phenyl)3-{[6-O-(6-deoxy-α-mannopyranosyl)-β-D-gluco-pyranosyl]oxy}-5,7-dihydroxy-4H-1-benzopyran-4-one. However, it is also known, for-example, under the names sophorin, birutan, rutabion, tarutin, phytomelin, melin or rutoside.

Rutin, with three molecules of water of crystallization, forms pale yellow to greenish needles. Anhydrous rutin has the properties of a weak acid, becomes brown at 1250° C. and decomposes at 214–2150° C. Rutin, which occurs in many plant species—frequently as an associate of vitamin C —, e.g. in citrus species, in yellow pansies, forsythia and acacia species, various Solanum and Nicotiana species, capers, lime blossom, St. John's wort, tee etc. was isolated from the common rue (Ruta graveolens) in 1842. Rutin can also be obtained from the leaves of buckwheat and of the east-asiatic pagoda tree Wei-Fa (Sophora japonica, Farbaceae), which contains 13–27% of rutin.

For the abovementioned reasons, it is desirable to prepare both rhamnose and monoglycosidated flavonoids from natural raw materials, for example from flavonoids having a bisglycosidic unit. In this connection, for example, the cleavage of rutinosides to rhamnose and the corresponding glucopyranosides is of interest.

Enzymatically catalyzed preparations of rhamnose are described in the literature. For example, EP 0 317 033 describes a process for the preparation of L-rhamnose, with the rhamnosidic bonding of glycosides which contain rhamnose bonded in the terminal position being achieved by enzymatic hydrolysis. However, cleavages of this type carried out in aqueous media of glycosides having a bisglycosidic structure of the carbohydrate radical usually proceed with low selectivity. For example, on account of the bisglycosidic structure of the carbohydrate radical in rutin, a mixture of the two monosaccharides glucose and rhamnose usually results. Moreover, high proportions of the aglycone quercetin and other undesired by-products usually occur.

In addition, enzymatically catalyzed cleavages of rutin are also described, for example, in JP 01213293. However, reactions of this type carried out in aqueous media usually likewise proceed with low selectivity.

The object was therefore to develop a process for the enzymatic cleavage of rutinosides to obtain rhamnose and/or the corresponding glucopyranosides which avoids or at least diminishes the disadvantages of the known processes and in particular makes possible a preparation of rhamnose and the glucopyranosides which is as selective as possible, so that these products can be prepared in high yield.

Surprisingly, it has now been found that this object is achieved if the process for the enzymatic cleavage of rutinosides to obtain rhamnose and/or the corresponding glucopyranosides is carried out such that the reaction takes place in the presence of a solvent mixture of water and one or more organic solvents.

The process according to the invention is distinguished in particular in that the cleavage of rutinosides to rhamnose and the corresponding glucopyranosides takes place with high selectivity. Rhamnose and the glucopyranosides are preferably obtained by suitable work-up after the process according to the invention. Furthermore, however, either only rhamnose or only the glucopyranosides can also be obtained by suitable work-up after the process according to the invention.

The present invention makes available an advantageous process for the enzymatic cleavage of rutinosides to obtain rhamnose and/or the corresponding gluco-pyranosides. According to this process, the rutinoside is contacted with a catalytic amount of an enzyme in a solvent mixture of water and one or more organic solvents. Preferably, the reaction is carried out with thorough mixing, e.g. by stirring.

The reaction is preferably carried out under a nitrogen atmosphere.

Suitable rutinosides for the process according to the invention are, for example, rutinosides which, as a sugar-free constituent or aglycone, contain a 2-phenyl-4H-1-benzopyran-4-one parent structure which carries a radical of the formula (I) in position 3 and whose phenyl groups, apart from position 3, can also be mono- or polysubstituted by —OH or —O—$(CH_2)_n$—H, where n is 1 to 8.

n is preferably 1.

The substitution of the 2-phenyl-4H-1-benzopyran-4-one parent structure by —OH and/or —O—$(CH_2)_n$—H preferably occurs in positions 5, 7, 3' and/or 4'.

Particularly preferred rutinosides correspond to formula (IV)

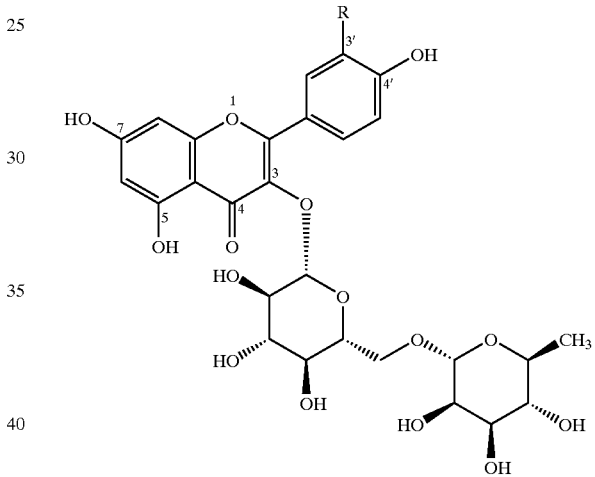

(IV)

in which R is H (kaempferol rutinoside), OH (rutin) or $OCH_3$ (isorhamnetin rutinoside). Rhamnose and kaempferol glucoside can be obtained from kaempferol rutinoside by the process according to the invention, rhamnose and isoquercetin from rutin, and rhamnose and isorhamnetin glucoside from isorhamnetin rutinoside. The rutinoside rutin is particularly preferably used.

The invention also relates to the use of kaempferol glucoside, isoquercetin and/or isorhamnetin glucoside in the foodstuffs and cosmetics industries.

The process according to the invention does not need any highly pure starting materials. For example, mixtures of rutinosides can also be used for the process according to the invention. The reaction also takes place, for example, if the starting material is contaminated with other flavonoids. It can also be carried out, for example, with mother liquor residues from rutin production.

Suitable enzymes for the process according to the invention are hydrolases. Hydrolases which have been obtained from the strain Penicillium decumbens are preferably used, in particular the enzymes naringinase and hesperidinase. The enzyme naringinase is very exceptionally preferred.

The starting materials and enzymes for the process according to the invention are commercially obtainable or can be obtained or prepared by methods which are well known to the person skilled in the art.

Suitable reaction temperatures for the process according to the invention are temperatures between 15 and 80° C. The process according to the invention is preferably carried out at reaction temperatures from 30 to 50° C., in particular at reaction temperatures from 35 to 45° C.

If the reaction temperature is too low, the reaction proceeds with an inappropriately slow reaction rate. In contrast, if the reaction temperature is too high, the enzyme, which is a protein, is denatured and thus deactivated.

Suitable pHs for the process according to the invention are pHs of between 3 and 8. The process according to the invention is preferably carried out at pHs from 4.5 to 7, in particular at pHs from 4.8 to 6.8. Furthermore, preferred pHs can however, vary, within the given limits depending on the enzyme used. For example, pHs from 6.4 to 6.8 are very exceptionally preferred when using the enzyme naringinase.

The process is preferably carried out in such a way that the pH is adjusted with the aid of a buffer system. In principle, all customary buffer systems which are suitable for the adjustment of the abovementioned pHs can be used. Preferably, however, aqueous citrate buffer is used.

Preferably, the preferred temperature and pH ranges are combined, i.e. the reaction is preferably carried out at a reaction temperature of 15 to 80° C. and at a pH from 3 to 8, particularly preferably at a reaction temperature of 30 to 50° C. and at a pH of 4.5 to 7 and particularly preferably at a reaction temperature of 35 to 45° C. and at a pH of 4.8 to 6.8.

The organic solvent(s) present in addition to water include (s) both organic solvents which are miscible with water and organic solvents which are not miscible with water.

Suitable organic solvents for the process according to the invention are nitriles such as acetonitrile, amides such as dimethylformamide, esters such as acetic acid esters, in particular methyl acetate or ethyl acetate, alcohols such as methanol or ethanol, ethers such as tetrahydrofuran or methyl tert-butyl ether and hydrocarbons such as toluene. Preferably, the process according to the invention is carried out in the presence of one or more of the organic solvents acetic acid esters, methanol, ethanol, methyl tert-butyl ether, toluene. Particularly preferably, the process according to the invention is carried out in the presence of one or more acetic acid esters, in particular in the presence of methyl acetate.

Suitable water:organic solvent volume ratios for the process according to the invention are ratios of 1:99 to 99:1. Preferably, the process according to the invention is carried out with water:organic solvent volume ratios of 20:80 to 80:20, in particular with volume ratios of 50:50 to 70:30.

Suitable weight ratios of rutinoside:(water+organic solvent) for the process according to the invention are ratios of 0.001:99.999 to 40:60. Preferably, the process according to the invention is carried out with weight ratios of rutinoside:(water+organic solvent) of 0.005:99.995 to 20:80, in particular with weight ratios of 0.5:99.5 to 10:90.

Suitable weight ratios of enzyme:rutinoside for the process according to the invention are ratios of 0.005:99.995 to 50:50. Preferably, the process according to the invention is carried out with weight ratios of enzyme rutinoside of 0.5:99.5 to 30:70, in particular with weight ratios of 2:98 to 20:80.

The progress or the end of the reaction can be checked, for example, by means of thin-layer chromatography (TLC).

After reaction is complete, the reaction mixture consists mainly of water, organic solvent, buffer (e.g. sodium citrate), enzyme, small amounts of unreacted rutinoside, rhamnose, glucopyranoside, small amounts of the aglycone of rutinoside and, if appropriate, small amounts of glucose. The desired reaction products rhamnose and glucopyranoside are isolated according to customary methods. "Customary work-up" in the context of the present invention is understood as meaning the following:

Preferably, the organic solvent is distilled off under reduced pressure. The glucopyranoside hereby crystallizing out, which can contain, for example, small amounts of the rutinoside and its aglycone, is separated off from the remaining reaction mixture, for example by suction filtration or filtration under reduced pressure or by centrifuging off the precipitated crystals. The solid is subsequently washed, preferably with water, and then dried. The purity of the glucopyranoside obtained when using pure rutinoside is customarily greater than 94%. For further purification, it can be recrystallized, for example, from suitable solvents, e.g. from water or from solvent mixtures consisting of toluene and methanol or consisting of water and methyl acetate.

Water, buffer, enzyme, small amounts of rutinoside, small amounts of its aglycone and, if appropriate, glucose as well as the desired reaction product rhamnose remain in the filtrate.

The isolation of the rhamnose remaining in the filtrate can be achieved by means of known processes, for example by ultrafiltration, by passing the filtrate over cation and/or anion exchangers, by crystallization and by means of mechanical separation, such as filtration. Glucose which may be present in the filtrate can also be removed, for example, by yeast fermentation.

The substances obtained in the work-up steps, such as the organic solvents, the enzyme or the buffer, for example sodium citrates, can be recirculated and thus used for further reactions.

The analysis of the reaction products can be carried out by HPLC, e.g. using standard HPLC equipment and columns containing reverse-phase materials with a $C_{18}$-alkyl coating.

The following examples are intended to illustrate the present invention. However, they are in no case to be considered as limiting.

EXAMPLES

The supply sources for the substances used are as follows:
Rutin: Merck KGaA, Item No. 500017
Naringinase: Sigma, Item No. N-1385
Hesperidinase Amano, Item No. HPV 12519

| | |
|---|---|
| Citric acid monohydrate | Merck KGaA, Item No. 100243 |
| Sodium hydroxide solution. | Merck KGaA, Item No. 105587 |
| Methyl acetate | Merck KGaA, Item No. 809711 |

The reaction is checked by means of thin-layer chromatography (TLC) and the reaction products are analyzed by means of HPLC.
TLC Conditions
Precoated TLC plates: Silica gel 60 (Merck KgaA, Item No. 105719),
Eluent: mixture of ethyl acetate ethyl methyl ketone: formic acid: water: 1-butanol in the volume ratio 50:30:10:10:5,
Spray reagent: iodine/sulfuric acid,
Detection: UV light (254 nm),
$R_f$ values:
   rutin: 0.38,
   isoquercetin: 0.61, quercetin: 0.96.
HPLC Conditions using a Standard HPLC Unit
Cartridge: LiChroCart® 2504/4 with
Column: LiChroSorb® RP18 (reversed phase material with $C_{18}$-alkyl coating and a particle size of 5 µm (Merck KGaA, Item No. 151355)),
Eluent: mixture of acetonitrile and water in the volume ratio 20:80 (pH 2; buffered with $NaH_2PO_4·H_2O/H_3PO_4$),
Flow: 1 ml/min,
Wavelength 260 nm,
Temperature: 30° C.,
Sample volume: 10 µl,
Sample preparation: dissolve 5 mg of the sample in 3 ml of methanol and make up to 10 ml with the eluent,
Reaction times:
  rutin: 7–7.5 min,
  isoquercetin: 8.5–9 min,
  quercetin: 40–43 min.

Example 1

3.15 g of citric acid monohydrate are dissolved in 150 ml of completely deionized water and adjusted to a pH of 6.6 using 10 g of 32% aqueous sodium hydroxide solution 150 ml of methyl acetate are subsequently added and 5.0 g of rutin and 0.5 g of naringinase are introduced under a nitrogen atmosphere with stirring (200 revolutions/minute). The reaction mixture is then stirred at a reaction temperature of 40° C. for 24 h. After customary work-up, rhamnose and 3.82 g of yellow crystals are obtained. The analysis of the yellow crystals by means of HPLC results in the following composition:
  Rutin: 1.2 area percent,
  Isoquercetin: 94.4 area percent,
  Quercetin: 2.6 area percent.

Example 2

0.32 g of citric acid monohydrate is dissolved in 150 ml of completely deionized water, and 150 ml of methyl acetate are added. The emulsion is subsequently adjusted to a pH of 5.0 using 2.5 g of 1 normal aqueous sodium hydroxide solution, and 5.0 g of rutin and 0.125 g of hesperidinase are introduced under a nitrogen atmosphere. The reaction mixture is then stirred (250 revolutions/minute) at a reaction temperature of 40° C. for 21 h. After customary work-up, rhamnose and 3.41 g of yellow crystals are obtained. The analysis of the yellow crystals by means of HPLC results in the following composition:
Rutin: 0.1 area percent,
Isoquercetin: 98.0 area percent,
Quercetin: 0.2 area percent.

Example 3

6.37 g of citric acid monohydrate are dissolved in 300 ml of completely deionized water and adjusted to a pH of 6.6 with 11.33 g of 32% aqueous sodium hydroxide solution. 300 ml of methyl acetate are subsequently added and 20.11 g of a starting material mixture which consists of 53.5 area percent of rutin, 39.8 area percent of isoquercetin and 0.4 area percent of quercetin (mother liquor residue from rutin production), and 1.11 g of naringinase are introduced under a nitrogen atmosphere. The reaction mixture is then stirred (200 revolutions/minute) at a reaction temperature of 40° C. for 46 h. After customary work-up, rhamnose and 14.18 g of yellow crystals are obtained. The analysis of the yellow crystals by means of HPLC results in the following composition:
Rutin: 0.5 area percent,
Isoquercetin: 92.0 area percent,
Quercetin: 4.7 area percent.

Comparison Example 12.6 g of citric acid monohydrate are dissolved in 600 ml of completely deionized water and adjusted to a pH of 6.6 with 40 g of 32% aqueous sodium hydroxide solution. 10.0 g of rutin and 1.0 g of naringinase are subsequently introduced under a nitrogen atmosphere with stirring (200 revolutions/minute). After stirring at 36° C. for about 24 hours, isoquercetin and rutin are present in the reaction mixture in a ratio of about 2:1. The reaction mixture is stirred at 36° C. for a further 7 h and at 40° C. for 22 h and then cooled to 15° C. After customary work-up, rhamnose and 7.25 g of yellow crystals are obtained. The analysis of the yellow crystals by means of HPLC results in the following composition:
Rutin: 12.1 area percent,
Isoquercetin: 76.6 area percent,
Quercetin: 10.5 area percent.

The Comparison Example shows that on use of water alone as solvent less solid (yellow crystals) is obtained, which moreover contains more starting material and more by-products than on use of a solvent mixture which consists of water and an organic solvent.

What is claimed is:

1. A process for the enzymatic cleavage of rutinosides to obtain rhamnose and/or the corresponding glucopyranosides, characterized in that the reaction is carried out in the presence of a solvent mixture of water and one or more organic solvents.

2. The process as claimed in claim 1, characterized in that the reaction is carried out at a reaction temperature of 15 to 80° C.

3. The process as claimed in claim 1, characterized in that the reaction is carried out at a pH from 3 to 8.

4. The process as claimed in claim 1, characterized in that the pH is adjusted with the aid of a buffer system.

5. The process as claimed in claim 4, characterized in that the pH is adjusted. with the aid of aqueous citrate buffer.

6. The process as claimed in claim 1, characterized in that the reaction is carried out in the presence of one or more of the organic solvents acetic acid esters, methanol, ethanol, methyl tert-butyl ester, toluene.

7. The process as claimed in claim 6, characterized in that the reaction is carried out in the presence of one or more acetic acid esters.

8. The process as claimed in claim 7, characterized in that the reaction is carried out in the presence of methyl acetate.

* * * * *